United States Patent
Hanoomanjee et al.

(10) Patent No.: US 8,650,961 B2
(45) Date of Patent: Feb. 18, 2014

(54) APPARATUS FOR GENERATING VIBRATIONS IN A COMPONENT

(75) Inventors: Sacheev D. Hanoomanjee, Derby (GB); Sophoclis Patsias, Stockport (GB)

(73) Assignee: Rolls-Royce PLC, London (GB)

( * ) Notice: Subject to any disclaimer, the term of this patent is extended or adjusted under 35 U.S.C. 154(b) by 386 days.

(21) Appl. No.: 12/987,468

(22) Filed: Jan. 10, 2011

(65) Prior Publication Data

US 2011/0179877 A1   Jul. 28, 2011

(30) Foreign Application Priority Data

Jan. 27, 2010 (GB) .................................. 1001284.7

(51) Int. Cl.
*G01M 7/02* (2006.01)

(52) U.S. Cl.
USPC .......................................... 73/662; 73/11.04

(58) Field of Classification Search
USPC ........... 73/662, 11.04, 11.09, 432.1, 574, 663
See application file for complete search history.

(56) References Cited

U.S. PATENT DOCUMENTS

| | | | | |
|---|---|---|---|---|
| 3,199,859 A | * | 8/1965 | Max Heynen et al. | 269/25 |
| 4,435,083 A | * | 3/1984 | Matson | 366/114 |
| 5,226,637 A | * | 7/1993 | Kitaura et al. | 269/234 |
| 5,287,027 A | * | 2/1994 | Marshall et al. | 310/21 |
| 5,669,742 A | * | 9/1997 | Sjoo et al. | 407/105 |
| 6,085,593 A | | 7/2000 | Pileri et al. | |
| 6,582,158 B1 | * | 6/2003 | Van Stein | 405/228 |
| 6,652,369 B2 | * | 11/2003 | Jones et al. | 451/365 |
| 6,890,248 B2 | * | 5/2005 | Whitmarsh et al. | 451/365 |
| 7,658,004 B2 | * | 2/2010 | Mielke | 29/889.7 |
| 2002/0017144 A1 | | 2/2002 | Miles et al. | |
| 2005/0091846 A1 | | 5/2005 | Powers et al. | |
| 2005/0252304 A1 | | 11/2005 | Woodward et al. | |
| 2005/0268728 A1 | | 12/2005 | Phipps | |

FOREIGN PATENT DOCUMENTS

| | | |
|---|---|---|
| CN | 201318986 Y | 9/2009 |
| EP | 0 506 385 A1 | 9/1992 |
| EP | 1 598 655 A2 | 11/2005 |
| EP | 1 602 914 A2 | 12/2005 |
| GB | 1 243 774 | 8/1971 |
| RU | 2 189 023 C2 | 9/2002 |
| SU | 574663 * | 10/1977 |
| SU | 657298 A1 | 4/1979 |
| SU | 1106630 * | 8/1984 |

(Continued)

OTHER PUBLICATIONS

Liddiard, "Tools for the Metallurgist," *Journal of Scientific Instruments*, 1965, pp. 522-523, vol. 42, No. 8, Institute of Physics Publishing, Bristol, Great Britain.

(Continued)

*Primary Examiner* — J M Saint Surin
(74) *Attorney, Agent, or Firm* — Oliff PLC

(57) ABSTRACT

An apparatus for generating vibrations in a component comprising a clamp assembly for clamping the component and a vibration generator for generating vibrations in the clamped component, the clamp assembly including: a base member, a pair of fixedly-spaced clamp members and a wedge for laterally wedging part of the component between the clamp members thereby to clamp the component. The base member, or a fixed clamp member, is inclined and the wedge having an inclined wedging surface arranged to engage the inclined base member or inclined fixed clamp member. The apparatus may form part of a test rig for vibration testing components such as turbo machine blades.

15 Claims, 2 Drawing Sheets

(56) References Cited

FOREIGN PATENT DOCUMENTS

| | | |
|---|---|---|
| SU | 1716374 A1 | 2/1992 |
| WO | WO 2009/007211 A1 | 1/2009 |
| WO | WO 2009/112795 A2 | 9/2009 |

OTHER PUBLICATIONS

Search Report issued in corresponding European Application No. 11 15 0455 dated Mar. 9, 2011.
Search Report issued in British Application No. GB 1001284.7 dated Mar. 8, 2010.

* cited by examiner

APPARATUS FOR GENERATING VIBRATIONS IN A COMPONENT

The present invention relates to apparatus configured for clamping a component, such as a gas turbine blade, and for generating vibrations in the clamped component, for example as part of a vibration test.

Vibration testing of components is commonplace in various fields. In the case of gas turbine blades, which include compressor blades, turbine blades and fan blades, vibration testing may be carried out to obtain the natural frequency of the blades or to analyse a stress distribution in the blades. In either case, the tests are typically carried out in order to validate a model for the blade, which may then be used as part of a whole engine model for modelling engine performance or the like. Vibration testing may also be carried out for other purposes: for example, fatigue testing to determine the life of a blade subject to high amplitude vibrations.

Various means may be used to generate the vibrations. For example, an electromagnetic shaker may be used for generating relatively high-amplitude vibrations, whereas a piezo-electric exciter may typically be used to generate relatively low-amplitude vibrations.

A problem associated with vibration testing of components is that of clamping the components sufficiently securely to allow accurate, controlled vibration of the component. The present invention seeks to address this problem.

According to the present invention an apparatus for generating vibrations in a component comprising a clamp assembly for clamping the component and a vibration generator for generating vibrations in the clamped component, the clamp assembly including: a base member, a pair of fixedly-spaced clamp members and a wedge for wedging part of the component between the clamp members thereby to clamp the component, wherein the base member, or a fixed clamp member, is inclined and the wedge having an inclined wedging surface arranged to engage the inclined base member or inclined fixed clamp member.

The first fixed clamp member may extend perpendicular to the base member, and a second, inclined, fixed clamp member extends away from the first fixed clamp member at an angle to the base, the wedge has an inclined wedging surface arranged to engage the second, inclined, fixed clamp member.

An adjustment bolt may be arranged to move the wedge along the second, inclined, fixed clamp member towards the base member and laterally towards the first fixed clamp member.

The clamp assembly may additionally comprise at least one clamp insert for wedging against said part of the component. In particular, the clamp assembly may comprise a pair of opposing clamp inserts for wedging the part of the component therebetween.

The wedge may be disposed between the clamp insert and a respective one of the clamp members. The wedge may be disposed between the clamp insert and the second, inclined, fixed clamp member.

Each clamp insert may be a fir-tree insert for engagement with part of a component incorporating a corresponding fir-tree portion, for example the root of a gas turbine blade.

The apparatus may comprise an electromagnetic shaker, in which case the fixed clamp members are mounted to a mass block for vibration by the electromagnetic shaker. Alternatively or additionally, the apparatus may comprise a piezo-electric exciter, with the fixed clamp members being mounted for vibration by the piezo-electric exciter.

The clamp assembly may comprise one or more shim elements for wedging between a respective insert and an adjacent clamp member or wedge.

The base member may be inclined, the first fixed clamp member and the second fixed clamp member have first and second inclined side walls respectively, the first and second walls are inclined in opposite directions, the wedge having an inclined wedging surface arranged to engage the inclined base member.

An adjustment bolt may be arranged to move the wedge along the inclined base member and towards the inclined side walls.

The apparatus may be a test rig for vibration testing gas turbine blades.

In a particular embodiment, the clamp assembly comprises a clamp frame defining a clamping channel, with the fixedly-spaced clamp members being formed by the opposing walls of the clamping channel. In this case, according to another aspect of the invention there is provided a method of clamping a component using the apparatus, the method comprising:

a) seating each clamp insert on a removable spacer insert located on the base of the clamping channel;

b) wedging the component laterally between the clamp members using the wedge; and c) removing the spacer insert to leave a clearance gap between each clamp insert and the base of the channel.

Embodiments of the invention will now be described, by way of example only, with reference to the accompanying drawings, in which.

Figure 3:
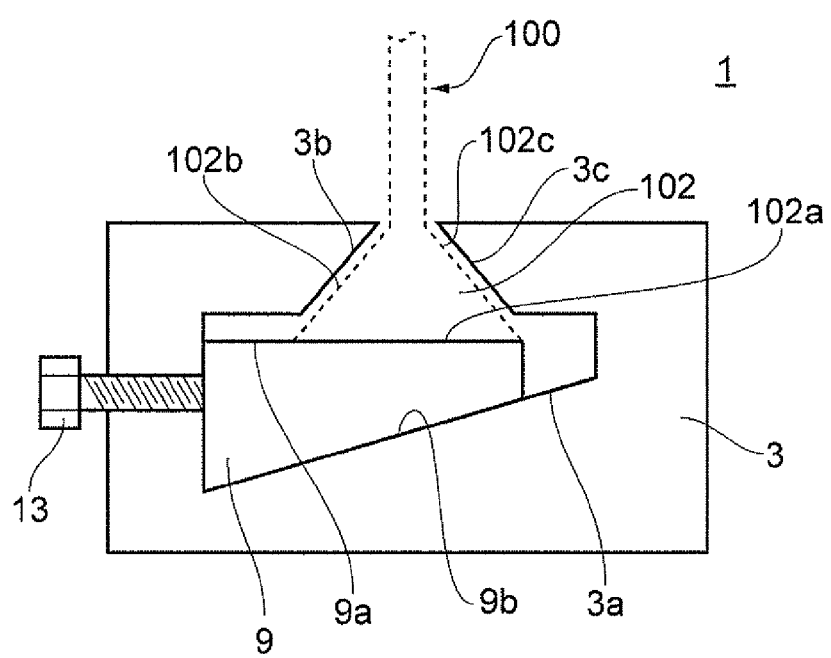

FIG. 3 schematically shows a second clamp assembly.

The clamp assembly 1 will in practice form part of a larger apparatus which is configured for generating vibrations in a component, in this case a test rig for vibration testing gas turbine blades. Unless otherwise indicated, it may be assumed that the parts of the test rig other than the clamp assembly illustrated in FIG. 1 may be conventional.

The clamp assembly 1 comprises four main components: a clamp frame 3, a first "fir-tree" clamp insert 5, a second "fir-tree" clamp insert 7 and a wedge 9.

The clamp frame 3 is a generally rigid component which defines a U-shaped clamping channel incorporating a base 3a, a first side wall 3b extending perpendicular to the base 3a, and a second, inclined side wall 3c extending away from the first side wall 3b at an angle α to the base 3a.

The clamp frame 3 is configured to be secured to a "mass block" (not shown) forming part of a conventional electromagnetic shaker. A series of securing bolts 11 running along either side of the U-shaped channel are provided for this purpose.

Each of the clamp inserts 5, 7 is an elongate element having a generally rectangular cross-section. The clamp inserts 5, 7 sit on the base 3a of the U-shaped channel, in between the opposing side walls 3b, 3c of the channel and extend generally lengthways along the channel, adjacent and generally parallel to one another. It should be noted that the clamp inserts 5, 7 sit "loosely" within the channel and are therefore free to move relative to one another and each of the side walls 3b, 3c of the channel. Each of the clamp inserts 5, 7 incorporates a respective "fir-tree" clamping face 5a, 7a configured for clamping engagement on opposite sides of a respective fir tree root portion on a gas turbine blade (not shown).

The wedge 9 is positioned in between the clamp insert 7 and the inclined side wall 3c. The wedge 9 is a "single-sided"

wedge having a "non-wedging" engagement surface 9a which engages the outer surface 7b of the clamp insert 7 (i.e. the surface of the clamp insert 7 opposite the fir-tree clamping surface 7a) and an inclined, "wedging" surface 9b which engages the inclined side wall 3c.

Figure 1:
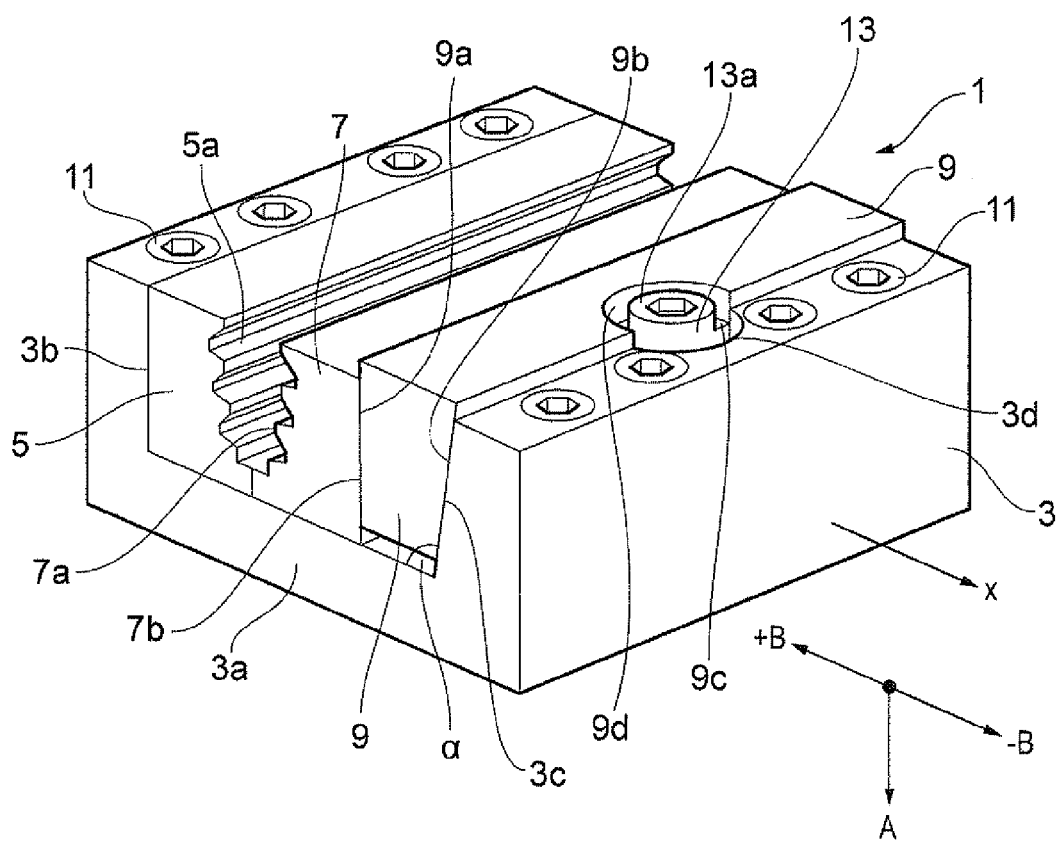
FIG. 1 is a schematic perspective view of a first clamp assembly.

It will be appreciated, referring to FIG. 1, that as the wedge 9 is driven downwardly in a 'radial' inward direction A, the wedging surface 9b cooperates with the inclined side wall 3c, thereby to move the non-wedging surface 9a laterally in the direction B. With the non-wedging surface 9a engaged with the respective outer surface 7b of the clamp insert 7, the wedge 9 may thus be used to move the clamp insert 7 in the direction B towards the other clamp insert 5, and to clamp the clamp inserts 5, 7 against opposite sides of the respective fir tree root portion on a gas turbine blade, thus laterally wedging the blade root securely between the clamp inserts 5, 7 and clamping the respective gas turbine blade in position. The adjustment bolt 13 is arranged to move the wedge 9 along the second, inclined, fixed clamp member 3c towards the base member 3a and laterally towards the first fixed clamp member 3b.

The wedge 9 may be advanced in the direction A by an adjustment bolt 13 which extends in the direction A through a clearance hole in the wedge 9 (not visible in FIG. 1) and screws into the base 3a of the clamp frame 3. The adjustment bolt 13 engages the wedge 9 by means of a respective bolt head 13a, which bears against a shoulder 9c formed by a counter bore 9d in the top surface of the wedge 9 (a respective, deeper, counter bore 3d is formed in the clamp frame 3 for allowing movement of the head 13a in the direction A, relative to the clamp frame 3, as the bolt 13 is screwed into the clamp frame 3).

In use, the clamp frame 3 is secured in position on the "mass block" of an electromagnetic shaker using the securing bolts 11, and the clamp assembly 1 is then used to clamp a suitable gas turbine blade conveniently as follows:

Firstly, the clamp inserts 5, 7 are arranged in the channel defined by the clamp frame 3, with the clamping surfaces 5a and 7a facing inwardly towards one another for engagement with a respective fir tree root portion on the gas turbine blade.

Following arrangement of the clamp inserts 5 and 7, the gas turbine blade—specifically, the fir tree root portion of the blade—is then inserted between the clamp inserts 5 and 7 and the adjustment bolt 13 is adjusted to drive the wedge 9 in the direction A, thereby laterally to wedge the blade root between the clamp inserts 5 and 7. The adjustment bolt 13 may be hand-tightened initially but it is envisaged that a torque wrench will be required to tighten the bolt to the necessary clamping torque.

It is envisaged that the clamp assembly 1 will provide for secure, stable clamping of a gas turbine blade.

More specifically, it will be noted that by utilising a wedge, the clamping force exerted by the clamp insert 5 and 7 can principally be directed laterally against the fir tree root of the gas turbine blade, (i.e. along the directions −B and +B respectively, parallel to the base 3a and perpendicular to the longitudinal axis of the fir tree root portion of the gas turbine blade), which cannot typically be achieved using prior art clamping arrangements.

The magnitude of the clamping force exerted by the clamp inserts 5, 7 will be determined in part according to the mechanical advantage afforded by the wedging surface 9b of the wedge 9 and the respective inclined side wall 3c of the clamp frame 3, which may conveniently be designed according to the specific application; in the case of a gas turbine blade being clamped for vibration testing in a test rig, for example, suitable results may be obtained by designing the wedging surface 9 and side wall 3c so that they provide a mechanical advantage of about 5 (assuming that the adjustment bolt 13 is tightened using a torque wrench and not merely hand-tightened).

Figure 2:
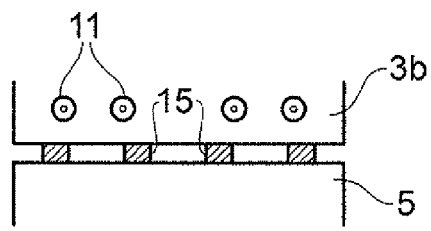
FIG. 2 is a plan view showing part of the clamp assembly of FIG. 1.

It should also be noted that the separate clamp inserts 5 and 7 may initially move relative to one another in a radial direction as the adjustment bolt 13 is being tightened, thus advantageously accommodating radial manufacturing tolerances in the blade root and promoting uniform radial loading along the clamping surfaces 5a, 7a. This initial 'radial' movement of clamp inserts 5, 7 may encompass a pivoting movement of the clamp inserts 5, 7 about an axis x (parallel to the clamping force exerted by the clamp inserts 5, 7).

Where it is desired to reduce the contact area between the clamp inserts 5, 7 and the clamp frame 3, for example to reduce frictional wear or friction damping, a spacer element may initially be seated underneath the clamp inserts 5, 7 on the base 3a of the clamp frame 3 and, following initial hand-tightening of the adjustment bolt 13, may subsequently be removed to create a clearance gap between the underside of the clamp inserts 5, and the base 3a. Additionally or alternatively, one or more strip elements or shims 15 (see FIG. 2) may be used to space the clamp insert 5 from the side wall 3b for similar reasons. The shims are preferably formed from a relatively soft material such as, for example, aluminium sheet.

The use of clamp inserts is not considered essential—it is envisaged that a component may be wedged directly between a wedge and a respective fixed clamp member—but use of inserts may be particularly advantageous for accommodating different sized and/or shaped components, in which case interchangeable clamp inserts may be used accordingly.

FIG. 3 shows a second type of clamp assembly, which in practice forms part of a larger apparatus configured for generating vibrations in a component, in this case a test rig for vibration testing compressor blades 100.

The clamp assembly 1 comprises a clamp frame 3, a wedge 9 and an adjustment bolt 13.

The clamp frame 3 defines a clamping channel incorporating an inclined base 3a and first and second fixedly spaced clamping members having first and second inclined side walls 3b, 3c respectively. The first and second side walls 3b, 3c are inclined in opposite directions. The wedge 9 is a "single-sided" wedge having a "non-wedging" engagement surface 9a and an inclined "wedging" surface 9b. The wedge 9 is located within the clamping channel with the inclined surface 9b of the wedge 9 in contact with the inclined base 3a of the clamping channel. The adjustment bolt 13 is located within a threaded hole in the clamping frame. As the bolt 13 is screwed into the threaded hole, the end of the bolt applies a lateral force to the wedge 9 and due to the inclined faces 9b, 3a of the wedge 9 and clamping channel, the wedge 9 moves in the radial direction towards the side walls 3b, 3c. The adjustment bolt 13 is arranged to move the wedge 9 along the inclined base 3a and towards the inclined side walls 3b, 3c.

In use, the dovetail shaped root portion 102 of a compressor blade 100 is located within the clamping channel. The first and second inclined side walls 3b, 3c correspond with the first and second inclined faces 102b, 102c of the root portion 102. The adjustment bolt 13 is screwed into the threaded hole which drives the non-inclined face 9a of the wedge 9 radially outwards. The non-inclined surface 9a applies a load to the base 102a of the root portion 102 which drives the blade 100 radially outward. The adjustment bolt 13 is tightened until the first and second inclined faces 102b, 102c of the root portion 102 are in intimate contact with the first and second side walls 3b, 3c of the clamping channel. In this configuration the root portion 102 is wedged between the first and second inclined side walls 3b, 3c of the clamp frame 3 by the wedge. This results in the blade 102 being securely clamped by the clamp assembly 1. The clamping assembly applies a base load to the dovetail portion of the compressor blade which helps to replicate the loading pattern which a compressor blade normally experiences.

The clamp assembly 1 described above can be attached to an electromagnetic shaker or any other type of suitable vibration generator in order to vibration test a blade.

Although the invention has been described with reference to gas turbines blades, the invention is not intended to be limited to any type of blade, or indeed any particular type of component.

The invention claimed is:

1. An apparatus for generating vibrations in a component, comprising:
    a clamp assembly for clamping the component; and
    a vibration generator for generating vibrations in the clamped component,
    the clamp assembly including:
        a base member,
        a pair of fixedly-spaced clamp members, and
        a wedge for wedging part of the component between the clamp members thereby to clamp the component,
    wherein the base member, or a first fixed clamp member, is inclined and the wedge having an inclined wedging surface arranged to engage the inclined base member or inclined fixed clamp member; and
    wherein the clamp assembly includes at least one clamp insert for wedging against the part of the component and one or more shim elements for wedging between a respective insert and an adjacent clamp member or wedge.

2. An apparatus according to claim 1, wherein the first fixed clamp member extends perpendicular to the base member, and a second, inclined, fixed clamp member extends away from the first fixed clamp member at an angle to the base member, the wedge has an inclined wedging surface arranged to engage the second, inclined, fixed clamp member.

3. An apparatus according to claim 2, wherein the wedge is disposed between the clamp insert and the second, inclined, fixed clamp member.

4. A method of clamping a component using the apparatus according to claim 2, wherein the clamp assembly comprises a clamp frame defining a clamping channel, with the fixedly-spaced clamp members being formed by the opposing walls of the clamping channel, and wherein the method comprises:
    a) seating each clamp insert on a removable spacer insert located on the base of the clamping channel;
    b) wedging the component laterally between the clamp members using the wedge; and
    c) removing the spacer insert to leave a clearance gap between each clamp insert and the base of the channel.

5. An apparatus according to claim 1, wherein the clamp assembly comprises a pair of opposing clamp inserts for wedging the part of the component therebetween.

6. An apparatus according to claim 1, wherein each clamp insert is a fir-tree insert for engagement with part of a component incorporating a corresponding fir-tree portion.

7. An apparatus according to claim 1, wherein the apparatus comprises an electromagnetic shaker and the fixed clamp members are mounted to a mass block for vibration by the electromagnetic shaker.

8. An apparatus according to claim 1, wherein the apparatus comprises a piezo-electric exciter and the fixed clamp members are mounted for vibration by the piezo-electric exciter.

9. An apparatus according to claim 1, wherein the clamp assembly comprises a clamp frame defining a clamping channel, with the fixedly-spaced clamp members being formed by the opposing walls of the clamping channel.

10. An apparatus according to claim 2, wherein an adjustment bolt is arranged to move the wedge along the second, inclined, fixed clamp member towards the base member and laterally towards the first fixed clamp member.

11. An apparatus according to claim 1, wherein the apparatus is a test rig for vibration testing gas turbine blades.

12. An apparatus as claimed in claim 1, wherein the shims are formed of a soft material.

13. An apparatus as claimed in claim 12, wherein the shims are formed of aluminium sheet.

14. An apparatus for generating vibrations in a component, comprising:
    a clamp assembly for clamping the component; and
    a vibration generator for generating vibrations in the clamped component,
    the clamp assembly including:
        a base member,
        a pair of fixedly-spaced clamp members, and
        a wedge for wedging part of the component between the clamp members thereby to clamp the component,
    wherein the base member is inclined and the wedge having an inclined wedging surface arranged to engage the inclined base member,
    wherein the first fixed clamp member and the second fixed clamp member have first and second inclined side walls respectively, the first and second walls are inclined in opposite directions, and
    wherein the wedge includes an inclined wedging surface arranged to engage the inclined base member.

15. An apparatus according to claim 14, wherein an adjustment bolt is arranged to move the wedge along the inclined base member and towards the inclined side walls.

* * * * *